United States Patent
Yoshiyama et al.

(10) Patent No.: US 7,838,640 B2
(45) Date of Patent: Nov. 23, 2010

(54) METHOD OF PRODUCING CELL EXTRACT FOR CELL-FREE PROTEIN SYNTHESIS

(75) Inventors: Yoshiko Yoshiyama, Yokohama (JP); Hirohisa Koga, Yokohama (JP)

(73) Assignee: Cellfree Sciences Co., Ltd., Kanagawa (JP)

( * ) Notice: Subject to any disclaimer, the term of this patent is extended or adjusted under 35 U.S.C. 154(b) by 841 days.

(21) Appl. No.: 10/591,754

(22) PCT Filed: Mar. 2, 2005

(86) PCT No.: PCT/JP2005/003508

§ 371 (c)(1),
(2), (4) Date: Sep. 1, 2006

(87) PCT Pub. No.: WO2005/083104

PCT Pub. Date: Sep. 9, 2005

(65) Prior Publication Data

US 2007/0134755 A1   Jun. 14, 2007

(30) Foreign Application Priority Data

Mar. 2, 2004   (JP) .............................. 2004-057373

(51) Int. Cl.
*A23J 1/00* (2006.01)
*C12P 1/00* (2006.01)
*C12P 21/06* (2006.01)
*C12P 21/04* (2006.01)

(52) U.S. Cl. ........................ 530/412; 435/41; 435/68.1; 435/69.1; 435/70.1; 435/71.1; 530/413

(58) Field of Classification Search ........................ None
See application file for complete search history.

(56) References Cited

FOREIGN PATENT DOCUMENTS

| JP | 5-236986 | 9/1993 |
| JP | 7-203984 | 8/1995 |

OTHER PUBLICATIONS

Hay et al. (Cell, vol. 89, 149-158, Apr. 4, 1997).*
Gonzalez et al. (A Novel Interaction between Perlecan Protein Core and Progranulin, The Journal of Biological Chemistry, vol. 278, No. 40, Issue of Oct. 3, pp. 38113-38116, 2003).*
Madin et al. (A highly efficient and robust cell-free protein synthesis system prepared from wheat embryos: Plants apparently contain a suicide system directed at ribosomes, PNAS, Jan. 18, 2000, vol. 97, No. 2, pp. 559-564).*
Zacharias et al. (Recombinant-protein solubility screening using the EasyXpress in vitro translation system, QIAGEN News 2004 e6, Retrieved from the Internet <URL:www1.qiagen.com/literature/qiagennews/weeklyArticle/04_02/e6/default.aspx>).*
Greene et al. (The Journal of Biological Chemistry vol. 278, No. 9, Issue of Feb. 28, pp. 7617-7623, 2003).*
Kimple et al. (Overview of affinity tags for protein purification, Curr Protoc Protein Sci., Sep. 2004, Chapter 9: Unit 9.9).*

* cited by examiner

*Primary Examiner*—Suzanne M Noakes
*Assistant Examiner*—Jae W Lee
(74) *Attorney, Agent, or Firm*—Wenderoth, Lind & Ponack, L.L.P.

(57) ABSTRACT

A cell extract for cell-free protein synthesis is produced by removing substances, which bind to an affinity support to be used in purification or interaction analysis, from a cell extract having protein synthetic activity. Then, a target protein is synthesized by using the cell extract for cell-free protein synthesis. The synthesized target protein can be purified by using the affinity support and used in interaction analysis.

5 Claims, 2 Drawing Sheets

US 7,838,640 B2

METHOD OF PRODUCING CELL EXTRACT FOR CELL-FREE PROTEIN SYNTHESIS

This application is a U.S. national stage of International Application No. PCT/JP2005/003508 filed Mar. 2, 2005.

FIELD OF THE INVENTION

The present invention relates to a cell extract for cell-free protein synthesis, a method of producing the cell extract, a method of synthesizing a target protein by using the cell extract, a method of purifying the synthesized target protein, and a method of analyzing an interaction between the synthesized target protein and a substance.

BACKGROUND ART

Known methods of synthesizing proteins include methods performed in living cells and methods performed in cell-free protein synthesis systems. A protein synthesized in any of those synthesis systems (hereinafter, also referred to as a "recombinant protein") can be utilized after purification with an appropriate method. Various methods for protein purification have been used depending on the types of proteins to be purified. Out of those methods, methods in which a protein to be synthesized is synthesized as a fusion protein having a peptide called "tag" using the synthesis system as described above and the purification of such a protein is then carried out by using an affinity support on which a substance that specifically binds to the tag peptide have been effectively used.

As a usage of a recombinant protein, for example, in the case of using it for the structural analysis and the like, an extremely high degree of purity of such a protein is required (see "Basic Experimental Techniques for Proteins and Enzymes", Nankodo Co., Ltd., 1981). In addition, when a recombinant protein is used in a functional analysis, one having a higher degree of purity is required. However, a target protein is rarely purified to a high degree even though the method of purifying a protein by using an affinity support as described above is performed, so that a combination of a plurality of purification has been required.

Such protein purification with a combination of plural kinds of purification methods is not only complicated in operation but also causes an increase in loss of a target protein in each purification step. Thus, there are problems in such a case as structural analysis where a large amount of protein is required.

Therefore, in order to solve those problems, a purification method having high purification efficiency has been desired.

Meanwhile, methods of performing interaction analysis between a protein and a substance have been used in general. However, if a target protein solution to be used in any of those methods contains substances which do not normally interact but bind nonspecifically, there are problems that a lot of pseudo-positive results are obtained and analytical efficiencies are very low in the case where a support or the like, which carries a substance with which the protein interacts, is allowed to contact with the protein to obtain the protein which binds to the substance. Therefore, a method of analyzing the interaction between a protein and a substance with high efficiency, which will solve those problems, has been desired.

DISCLOSURE OF THE INVENTION

An object of the present invention is to provide a method of purifying a protein with a high degree of purification efficiency and a method of analyzing interaction between a protein (polypeptide) and a substance with high efficiency. To be more specific, an object of the present invention is to provide a cell extract for cell-free protein synthesis, which synthesizes a protein to be used in the method of purifying a protein with a high degree of purification efficiency and in the method of analyzing the interaction between a protein and a substance with high efficiency, a method of synthesizing a protein using the cell extract, a method of purifying a protein synthesized by using the cell extract, and a method of analyzing the interaction between a protein and a substance by using the protein synthesized using the cell extract.

According to the present invention, the followings are provided.

(1) A method of producing a cell extract for cell-free protein synthesis, comprising the step of contacting a cell extract having a protein synthetic activity with an affinity support having an affinity to a protein to be synthesized using the extract, and removing substances bound to the affinity support from the cell extract, and wherein the affinity support does not impair the protein synthetic activity of the cell extract when the affinity support is contacted with the cell extract.

(2) The method according to (1), wherein the cell extract is a wheat germ extract.

(3) The method according to (1) or (2), wherein the affinity support immobilizes a substance which can bind to the protein synthesized using the cell extract for cell-free protein synthesis produced by the method according to (1) or (2).

(4) The method according to any one of (1) to (3), wherein the affinity support is a metal ion immobilized support.

(5) The method according to (4), wherein the metal ion immobilized support is a cobalt immobilized support, a nickel immobilized support, or a zinc immobilized support.

(6) A cell extract for cell-free protein synthesis, which is produced by the method according to any one of (1) to (5).

(7) A cell extract for cell-free protein synthesis, wherein substances, which bind to an affinity support having an affinity to a protein synthesized using the cell extract and have little influence on protein synthetic activity of the cell extract, are removed.

(8) A method of producing a protein, comprising synthesizing a protein by using the cell extract for cell-free protein synthesis according to (6) or (7).

(9) A method of purifying a protein, comprising:

performing protein synthesis reaction by using the cell extract for cell-free protein synthesis according to (6) or (7); and contacting the obtained synthesis reaction solution with an affinity support used in the production of the cell extract or with an affinity support which is substantially the same as the affinity support to allow the protein to bind to the affinity support, to thereby collect the protein.

(10) A method of analyzing an interaction between a protein and a substance, comprising:

performing protein synthesis reaction by using the cell extract for cell-free protein synthesis according to (6) or (7); and contacting the obtained synthesis reaction solution with the affinity support used in the production of the cell extract or with an affinity support which is substantially the same as the

BEST MODE FOR CARRYING OUT THE INVENTION

Figure 1:
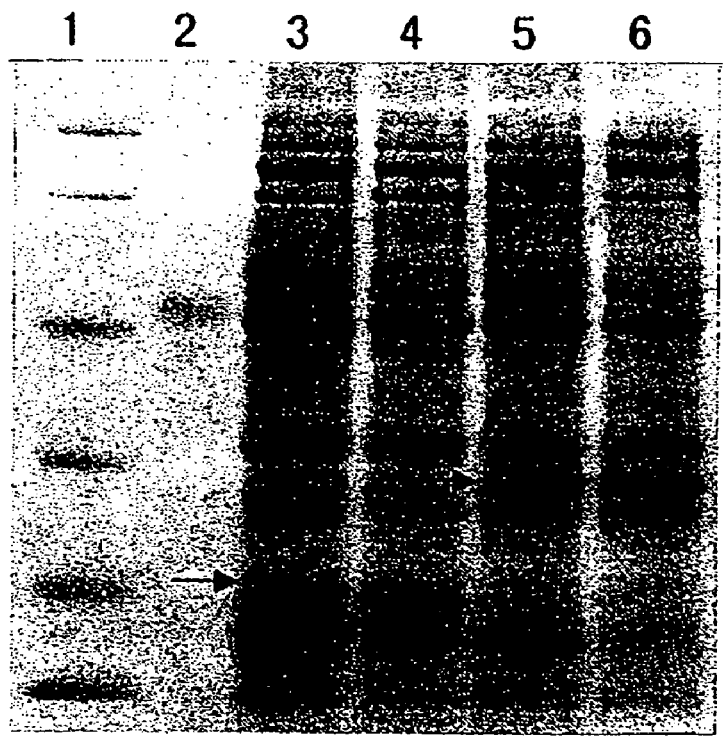
FIG. 1 is an electrophoretic photograph that shows the amounts of synthesized target proteins when a protein synthesis reaction is carried out by using a wheat germ extract treated with a Talon column or an untreated wheat germ extract. In the figure, lane 1 represents a marker, lane 2 represents creatine kinase as a control, lane 3 represents a result of a reaction solution in which N-His-JSP-1 was synthesized by using the untreated wheat germ extract, lane 4 represents a result of a reaction solution in which N-His-JSP-1 was synthesized by using the wheat germ extract treated with the Talon column, lane 5 represents a result of a reaction solution in which GFP was synthesized by using the untreated wheat germ extract, and lane 6 represents a result of a reaction solution in which GFP was synthesized by using the wheat germ extract treated with the Talon column. The protein synthetic ability of the wheat germ extract treated with the Talon column is approximately equivalent to that of the untreated wheat germ extract.

Hereinafter, the best mode for carrying out the present invention will be described in detail. The explanation about the constitutions as described below is about the examples (representative examples) of embodiments of the present invention, so that the present invention is not limited thereto.

(1) Production of Cell Extract for Cell-Free Protein Synthesis

One aspect of the present invention is a method of producing a cell extract for cell-free protein synthesis. The method comprises the step of contacting a cell extract having a protein synthetic activity with an affinity support having an affinity to a protein to be synthesized using the extract to remove substances, which bind to the affinity support, from the cell extract, and the affinity support does not impair the protein synthetic activity of the cell extract even when the affinity support is contacted with the cell extract. The phrase "a cell extract having a protein synthetic activity" means a cell extract that is capable of carrying out cell-free protein synthesis when it is provided with template nucleic acids, amino acids, an energy source, and the like, and it includes any of cell extracts having such an activity (hereinafter, also referred to as a "cell extract"). To be specific, examples of the cell extracts include those from *Escherichia coli*, germ of plant seeds, and rabbit reticulocytes, and the like. Those cell extracts for cell-free protein synthesis may be commercially available or may be prepared by any of methods known in the art. For example, in a case of *Escherichia coli*, it may be prepared by using a method described in Pratt, J. M. et al., Transcription and translation, Hames, 179-209, B. D. & Higgins, S. J., IRL Press, Oxford (1984).

Examples of the commercially available cell extracts for cell-free protein synthesis which can be used include *E. coli* S30 extract system (Promega) as one derived from *Escherichia coli*, Rabbit Reticulocyte Lysate System (Promega) as one derived from rabbit reticulocytes, and PROTEIOS™ (TOYOBO) as one derived from wheat germ.

In a case where a metal ion immobilized support is used in the purification of a target protein which is synthesized using the wheat germ cell extract, it is preferable to use the wheat germ cell extract for cell-free protein synthesis produced by the method of the present invention, because many substances which bind to the metal ion immobilized support are contained in the wheat germ cell extract.

As a wheat germ cell extract, which can be used as a raw material in the method of producing a cell extract for cell-free protein synthesis of the present invention, a cell extract prepared by the method described in WO 03/064671 or the like is particularly preferably used.

To be more specific, a wheat-germ cell extract can be prepared in the following manner:

A germ fraction mainly composed of intact germ is collected from wheat seeds. In this case, the term "intact germ" means a germ having at least germinability, and the term "germ fraction" means a fraction that contains intact germ as a main component and from which a cell extract which can be used in the cell-free protein synthesis can be prepared. As the amount of germ contained in plant seeds is small, it is desirable to eliminate, to as great an extent as is possible, components other than germ, so as to recover the germ efficiently. Normally, mechanical force is first applied to the plant seeds so as to produce a mixture comprising germ, crushed endosperm and crushed seed coat. The crushed endosperm, crushed seed coat and the like are removed from this mixture, so as to produce a crude germ fraction (a mixture primarily composed of germ but also containing crushed endosperm and crushed seed coat). It suffices that the force applied to the plant seed is of a strength sufficient to separate the germ from the plant seed.

Normally, conventional grinding equipment is used to grind the plant seeds, so as to produce a mixture containing germ, crushed endosperm and crushed seed coat. The plant seeds can be ground using commonly known grinding apparatus but it is preferable to use grinding apparatus of the type that applies impact force to the material that is ground, such as a pin mill or a hammer mill. The degree of grinding may be suitably chosen according to the size of the germ of the plant seed that is used. For example, wheat grain is usually ground to a maximum length of no greater than 4 mm, and is preferably ground to a maximum length of no greater than 2 mm. Furthermore, it is preferable that the grinding is performed by dry grinding.

Next, a crude germ fraction is recovered from the ground plant seed produced, using classifier well-known per se, such as a sieve. For example, in the case of wheat grain, a crude germ fraction is normally recovered using a mesh size of 0.5 to 2.0 mm, and preferably 0.7 to 1.4 mm. Furthermore, if necessary, the seed coat, endosperm, dust and the like contained in the crude germ fraction produced can be removed by wind force or electrostatic force.

It is also possible to produce a crude germ fraction by using methods that make use of the difference in the specific gravities of germ, seed coat and endosperm, such as heavy media separation. In order to obtain a crude germ fraction containing a greater quantity of germ, a plurality of the methods described above may be combined. The germ is harder than any other part than the germ, so that the parts other than germ can be ground in the above grinding treatment, while the germ is not ground and can be separated while maintaining its shape.

From the crude germ fraction containing germ, endosperm debris, seed-coat debris, and the like obtained as described above, germ is separated on the basis of the difference in shape from other components by visual observation or the like. Germ may be separated from seed-ground product, however, such a separation method is not efficient because the seed-ground product contains large amounts of components other than germ. As the endosperm component may adhere to the germ fraction produced in this manner, it is preferable that this be washed in order to purify the germ. It is preferable that this is washed by dispersing/suspending the germ fraction in cold water or a cold aqueous solution at a temperature that is normally no greater than 10° C. and preferably no greater than 4° C. and washed until the washing solution is no longer clouded. It is more preferable that the germ fraction be dispersed/suspended in an aqueous solution containing a detergent, which is normally at a temperature of no more than 10° C. and preferably at a temperature of no more than 4° C., and washed until the washing solution is no longer clouded. It is preferable that the detergent is nonionic, and a wide variety of detergents can be used so long as these are nonionic. Specific examples of suitable substances include Brij, Triton, Nonidet P40, Tween, and the like, which are polyoxyethylene derivatives. From among these, Nonidet P40 is the most suitable. These nonionic detergents can, for example, be used at a concentration of 0.5%. The washing treatment may be either one of washing with water or an aqueous solution, or washing with a detergent. Alternatively, the two may be used together. Furthermore, this washing may be combined with a supersonic treatment.

Consequently, the germ fraction from which the endosperm component has been removed can be obtained. The absence of the endosperm component in the germ fraction can be confirmed by the fact that ribosomes cannot be substantially deadenylated with trichine.

The germ obtained as described above is subjected to fine-grinding and extraction treatment, thereby a germ extract can be obtained. A method of obtaining a germ extract may be any of the conventional methods. For instance, germ that is frozen in liquid nitrogen is finely ground by using a mortar or the like, and then added with an extraction solvent and stirred, and subsequently, a liquid containing a germ extract is collected by centrifugation or the like, and followed by purification through a gel filtration or the like. Alternatively, the germ may be ground by means of an impact or cutting, and then added with an extraction solvent and stirred, and subsequently, a liquid containing a germ extract is collected by centrifugation and followed by purification through a gel filtration or the like.

For extraction solvents, an aqueous solution containing buffer, potassium ion, magnesium ion and/or an antioxidant for a thiol group may be used. In addition, if required, the solution may be further added with calcium ion, L-amino acids, and the like. For instance, a solution containing N-2-hydroxyethylpiperazine-N'-2-ethanesulfonic acid (HEPES)-KOH, potassium acetate, magnesium acetate, L-amino acids, and/or dithiothreitol, or a solution prepared by partially modifying a method of Patterson et al. (i.e., a solution containing HEPES-KOH, potassium acetate, magnesium acetate, calcium chloride, L-amino acids, and/or dithiothreitol) can be used as an extraction solvent. The composition and concentration of each component in the extraction solvent is known in the art, so that one which can be used in the method of producing a wheat germ extract for cell-free protein synthesis may be used.

A gel filtration can be carried out by, for example, using a gel filtration apparatus which has been previously equilibrated with an extraction solvent (containing HEPES-KOH, potassium acetate, magnesium acetate, dithiothreitol, or L-amino acids). The composition and concentration of each component in a gel-filtration solution are known in the art, so that one which can be used in the method of producing a wheat germ extract for cell-free protein synthesis may be employed.

In the present invention, the term "affinity support" means a support that carries a substance having a property that it has an affinity to a specific protein and binds to such a protein and adsorbs the protein thereon. The affinity support can be used in the purification of a specific protein or any of other proteins through the specific protein by binding and adsorbing the specific protein thereon. In addition, an affinity support that carries such a substance that interacts with a specific protein is used in the analysis of interaction between the specific protein and a substance. In the method of the present invention, an affinity support having an affinity to a protein to be synthesized by using the cell extract for cell-free protein synthesis of the present invention is used.

In the method of the present invention, the "substances bound to an affinity support", which are removed from a cell extract, may be any of substances as long as it is contained in the cell extract before being contacted with the affinity support, and binds to the affinity support and the protein synthetic activity of the cell extract is retained without loss even when the substance is removed from the cell extract having a protein synthetic activity. In addition, the phrase "the protein synthetic ability of the cell extract is retained" means that the protein synthetic ability of the cell extract is retained in such an extent that a target protein can be synthesized in an amount sufficient to be utilized. To be specific, it means that, the protein synthetic ability is retained not less than 30%, preferably not less than 50%, and more preferably not less than 70% as compared with that of the same extract but untreated. Those cell extracts include one having an increased protein synthetic ability as compared with that of the untreated cell extract. For instance, the protein synthetic ability can be determined by comparing the band-density of a synthesized protein by electrophoresis such as SDS-PAGE, or comparing the amounts of a labeled amino acid incorporated into a synthetic protein after adding the labeled amino acids into a synthesis reaction system.

Specific examples of the affinity supports, which are commonly used in the purification of proteins, include: metal ion immobilized supports such as a cobalt immobilized support and a nickel immobilized support and the like; metal ion immobilized supports composed of the combination of metal ion immobilized supports such as HiTrap chelating HP (Amersham) and IPAC Metal Chelating Resin (Eprogen) and the like, and metal ions such as a nickel ion, a cobalt ion, and a zinc ion and the like; antibody-immobilized support; maltose-immobilized support; glutathione-immobilized support; methotrexate-immobilized support; protein G-immobilized support; protein A-immobilized support; antibody Fc region-immobilized support; 4-aminophenylarsine oxide-immobilized support; and cellulose-immobilized support and the like. In addition, examples of the antibody-immobilized supports include anti-HA-antibody-immobilized support, anti-FLAG-antibody-immobilized support, anti-myc-tag-antibody-immobilized support, anti-T7-antibody-immobilized support, anti-V5-antibody-immobilized support, anti-thioredoxin-antibody-immobilized support, anti-CAT-antibody-immobilized support, anti-GFP-antibody-immobilized support, and anti-β-gal antibody-immobilized support, and the like.

Preferable combinations of the above-described cell extract and affinity support include a combination of the wheat germ extract and any of metal ion immobilized supports, a combination of the wheat germ extract and the glutathione-immobilized support, and the like. Preferable examples of the metal ion immobilized support include the cobalt immobilized support and the nickel immobilized support. To be more specific, the cobalt immobilized support may be Talon Metal Affinity Resin (Clontech Laboratories, BD Bioscience), and examples of the nickel immobilized support include Ni-NTA-Agarose (Qiagen) and Ni-Sepharose (Amersham).

Meanwhile, examples of supports used for analyzing the interaction between a protein and a substance include those that carry a substance, which binds to specific proteins, such as pharmaceutically active compounds, enzyme-inhibiting substances, ATP analogs, nucleic acids, proteins, and polypeptides and the like.

The support that constitutes an affinity support, and carries a substance having an affinity to a protein may be any of those that can be used in the method of the present invention, such as production of a cell extract, purification of proteins, or analysis of interaction between a protein and a substance, or the like. Specific examples thereof, which are preferably used, include balls, beads, gears, microplates and the like which are made of agarose, cellulose, sepharose, polystyrene, polyethylene, polyacrylate, Teflon, polyacetal, or the like. An immobilization method may be any of those known in the art.

The affinity support used in the method of the present invention may be selected on the basis of a criterion that the protein synthetic ability of the cell extract is retained without loss even if it is contacted with a cell extract to remove substances that bind to the affinity support from the cell extract. To be specific, for example, a target protein is synthesized by a method as described below by using the cell extract after contacting the cell extract with an affinity support by a method as described below (hereinafter, such an operation may be referred to as "adsorption"). Here, there is provided a method in which, by comparing the amount of the synthesized target protein with the amount of the target protein synthesized using an untreated cell extract by an appropriate method, the target protein having a synthesized amount of not less than 30%, preferably not less than 50%, and more preferably not less than 70% as compared with one synthesized using the untreated cell extract is selected.

The method of producing a cell extract for cell-free protein synthesis of the present invention is characterized by comprising a step of contacting the cell extract with the affinity support. The "method of contacting the cell extract with the affinity support" may be suitably selected depending on the types of the affinity support and the cell extract. However, it is preferable to contact under the same conditions as those of the purification or interaction analysis of the protein synthesized from the cell extract for cell-free protein synthesis of the present invention by using the affinity support. However, it is important to contact such that the protein synthetic ability of the cell extract is retained. In addition, the volume of the affinity support and the cell extract to be brought into contact with each other may be suitably selected depending on their types, and the affinity support is preferably used in a volume of $\frac{1}{100}$ fold or more with respect to the cell extract, and more preferably in a volume of $\frac{1}{10}$ to 10 fold, and most preferably in a volume of $\frac{1}{5}$ to 2 fold with respect to the cell extract.

Specific methods of contacting the cell extract with the affinity support include a batch method in which the affinity support and the cell extract are mixed together in an appropriate container, a column method in which the cell extract is loaded into an appropriate column after loading an affinity support into the column, and the like. In a case of using the column method, the affinity support is preferably equilibrated with an appropriate buffer in advance. The appropriate buffer is appropriately selected depending on the type of the affinity support to be used, and it is preferably replaced with the same buffer as that of the cell extract before addition of the cell extract.

The temperature at which the contact is carried out may be within a range in which substances in a cell extract, which bind to an affinity support, are allowed to bind to the affinity support, and the protein synthetic ability of the cell extract is retained. To be specific, for example, the range is preferably from 0 to 50° C., and more preferably 2 to 30° C. In particular, when a wheat germ extract is used as a cell extract, the contact is preferably carried out at 4 to 26° C. The contact may be carried out for any time period as far as it allows substances in the cell extract, which bind to the affinity support, to bind to the affinity support, and the protein synthetic activity of the cell extract does not decrease. To be specific, for example, it is 1 minute or more, preferably 5 to 100 minutes, and more preferably 10 to 60 minutes.

When the metal ion immobilized support is used, a metal may be released from the support depending on the concentration of a reductant, particularly dithiothreitol in the cell extract, and, the metal ion immobilized support can be used as far as the released metal does not extensively affect the protein synthetic activity. In addition, it is advantageous to adjust the concentration of the reductant, or use another reductant, or the like to inhibit such release of metal. Further, when the metal ion immobilized support is brought into contact with the cell extract, the adsorption of substances which non-specifically and weakly bind to the metal ion immobilized support can be inhibited by adding a compound having an imidazole ring, such as imidazole, or a derivative thereof (hereinafter, also referred to as "imidazoles"), which is effective to retain the protein synthetic ability of the cell extract for cell-free protein synthesis of the present invention. To be specific, the concentration of imidazoles is exemplified by 1 mM or more, preferably 2 to 50 mM, and more preferably 10 to 20 mM.

Furthermore, the contact between the cell extract and the affinity support may be carried out after completion of all the steps for preparing a known cell extract, or at any of steps after extraction of an extract having protein synthetic activity from cells.

Therefore, the cell extract for cell-free protein synthesis of the present invention, which is produced as described above, is also within the scope of the present invention. The cell extract for cell-free protein synthesis of the present invention is characterized in that substances, which bind to an affinity support having an affinity to a specific protein and do not significantly cause an influence on the protein synthetic ability of the cell extract, are removed.

The cell extract for cell-free protein synthesis of the present invention may be added with a template for translation, nuclease inhibitors, various kinds of ions, substrates, energy sources and the like, which are required for protein synthesis (hereinafter, also referred to as "additives for translation reaction") to provide a synthetic system (kit) for a target protein, thereby allowing the synthesis of a protein. In addition, the cell extract for cell-free protein synthesis of the present invention is concentrated by using an appropriate apparatus and then can be used for the synthesis of a target protein. The cell extract for cell-free protein synthesis of the present invention may be frozen and stored, or may be stored as a liquid that is added with additives for translation reaction except the translation template and nuclease inhibitors (herein also referred to as "ready-made cell extract"). Furthermore, it may be freeze-dried and stored by using the method as described in JP-A-2000-316594, JP-A-2002-125693, or the like. The phrase "does not significantly cause an influence on the protein synthetic ability of the cell extract" means that, when the substance is removed from the cell extract, the protein synthetic ability thereof is not less than 30%, preferably not less than 50%, more preferably not less than 70%, as compared with that of the untreated cell extract.

(2) Synthesis of Target Protein

Protein synthesis can be performed by adding the above mentioned additives for translation reaction to the cell extract for cell-free protein synthesis produced by the method as described in the above section (1) to provide a system for synthesis of a target protein. The additives for translation reaction may be different depending on the cell extract for cell-free protein synthesis to be used, however, any of those known in the art can be appropriately chosen and used.

To be specific, for example, when a wheat germ extract is used, a translation reaction solution contains nucleic acids as a template, amino acids as substrates, energy sources, various kinds of ions, buffer, ATP-regenerating system, nuclease inhibitors, tRNAs, a reductant, polyethylene glycol, 3',5'-cAMPs, folate, an antibacterial agent, and the like. These additives are preferably contained at their respective concentrations: 100 µM to 0.5 mM for ATP, 25 µM to 1 mM for GTP, and 25 µM to 0.4 mM for each of 20 different amino acids. In a case where a wheat germ extract prepared by the method as described in WO 03/064671 is used as a cell extract, generally, there is no need to add tRNA.

The method or device for protein synthesis can be selected from those known in the art, each of which is suitable for a selected cell extract for cell-free protein synthesis. When a wheat germ extract is used, a method in which energy sources, amino acids, or tRNAs required for cell-free protein synthesis are added to the cell extract for cell-free protein synthesis of the present invention, such as a batch method (Pratt, J. M. et al., Transcription and Translation, Hames, 179-209, B. D. & Higgins, S. J., eds, IRL Press, Oxford (1984)), a continuous cell-free protein synthetic system in which amino acids, energy sources, and the like are continuously supplied to the reaction system (Spirin, A. S. et al., Science, 242, 1162-1164 (1988)), a dialysis method (Kigawa et al., 21th Annual Meeting of Molecular Biology Society of Japan, WID6), a bilayer method (Sawasaki, T. et al., FEBS Let., 514, 102-105 (2002)), or the like can be used. Further, a discontinuous gel filtration method (JP-A-2000-333673) or the like can be used, in which a template RNA, amino acids, energy sources, and the like are supplied as needed and a synthetic product and decomposed product are discharged as needed. Furthermore, a method in which a translation reaction solution is superimposed on the upper part of a sol or gel that contains amino acids, energy sources, and the like required for the cell-free protein synthesis can be used (WO 2004/050891).

Nucleic acids used as a template are one that encodes a target protein. The target protein may be any protein that can be synthesized in the cell extract of the present invention. However, the advantage of using the cell extract of the present invention is exerted in the purification of the target protein and the analysis of the interaction between the target protein and a substance, so that a preferable protein may be one that has an affinity to a substance carried on an affinity support and binds to the substance. When the target protein is purified, it is necessary that the protein binds to the substance carried on the affinity support. In this case, when a target protein does not bind to the affinity support used in the production of the cell extract for cell-free protein synthesis of the present invention or one used in the purification of the target protein as described below, nucleic acids that encode a fusion protein comprising a peptide capable of binding to the affinity support (hereinafter, also referred to as a "tag") can be used.

To be specific, the nucleic acids preferably have a nucleotide sequence that encodes the target protein or a nucleotide sequence that encodes a fusion protein comprising the target protein and the tag (hereinafter, also referred to as "ORF"), and also has a transcription/translation-controlling region such as a promoter sequence, a translation activity enhancement sequence, and the like at the upstream of ORF, and a termination sequence and a non-translated region for mRNA stability at the downstream. The promoter sequence can be appropriately selected depending on the cell extract for cell-free protein synthesis of the present invention or an RNA polymerase used for transcription. To be specific, when SP6 RNA polymerase is used for transcription, an SP6 promoter is preferably used. Specific examples of the translation activity enhancement sequence include a 5'-cap structure (Shatkin, Cell, 9, 645- (1976)), a Kozak's sequence (Kozak, Nucleic Acid. Res., 12, 857- (1984)) in a eukaryote, and a Shine-Dalgarno sequence in a prokaryote. Further, it is known that a 5'-nontranslated leader sequence of RNA virus also has a translation-promoting activity (Japanese Patent No.

2814433) and a method of effectively carrying out protein synthesis using such a sequence has been developed (JP-A-10-146197).

The target protein may be any of proteins that can be synthesized by the above-mentioned synthetic method using the cell extract for cell-free protein synthesis of the present invention. When a fusion protein comprising a tag is used as a target protein, the tag to be used is one having a property of specifically binding to the above-mentioned affinity support. Examples of the combination of a affinity support used in the present invention and a tag specifically binding to the affinity support include: a metal ion immobilized support and polyhistidine; a maltose-immobilized support and a maltose-binding protein; a glutathione-immobilized support and a glutathione-S transferase (GST); a methotrexate-immobilized support and a dihydrofolate reductase (DHFR); a Protein G-immobilized support or Protein A-immobilized support and an Fc region of an antibody; an antibody Fc region-immobilized support and a Protein G or Protein A; a 4-aminophenylarsine oxide-immobilized support and thioredoxin; a cellulose-immobilized support and a cellulose-binding region; an anti-HA antibody-immobilized support and an HA tag; an anti-FLAG antibody-immobilized support and a FLAG tag; an anti-myc antibody-immobilized support and a myc tag; an anti-T7 antibody-immobilized support and a T7 tag; an anti-V5 antibody-immobilized support and a V5 tag; an anti-thioredoxin antibody-immobilized support and thioredoxin; an anti-CAT antibody-immobilized support and a CAT tag; and an anti-GFP antibody-immobilized support and a GFP.

Any of these tags may be contained in any part of the target protein, and it may preferably be positioned at the N- or C-terminal of the target protein. When any of the antibody-immobilized supports listed in the above section (1) is used in the production of the cell extract for cell-free protein synthesis of the present invention, or in the purification of a target protein, a fusion protein comprising an antigenic polypeptide against such an antibody and the target protein can be used. Here, when the antigen against the antibody immobilized on the support is the target protein itself, the target protein itself can be used. The structure of the antigenic polypeptide to be used as a tag is not particularly limited as far as it can bind to an antibody carried on the support.

Further, when an avidin-immobilized support or a streptoavidin-immobilized support is used in the production of the cell extract for cell-free protein synthesis of the present invention or the purification of a target protein, a synthetic method in which the target is labeled with biotin is used. To be specific, for example, a method, in which biotinylated amino acids and a template that encode a target protein is used.

Further, if required, a template, which has a structure for cleaving the tag from the target protein after purification of the target protein using the affinity support, can be used. To be specific, a template that encodes a protein in which a protease-recognition sequence is inserted between the tag and the target protein can be used. To be specific, an example of the protease-recognition sequence may be a PreScission™ Protease (Amersham Bioscience, Co., Ltd.) recognition sequence, and the like.

Further, when the protein synthesized using the cell extract of the present invention is used in the analysis of the interaction between a protein and a substance, a protein to be synthesized is preferably synthesized so as to have a form suitable for the interaction analysis. To be specific, for example, it may be a molecule having a form in which a protein (polypeptide) is covalently bound to nucleic acids that encode the protein, and the like. A synthetic method of such a molecule, and a method of analyzing the interaction between a protein and a substance using such a molecule can be carried out by using the method as described in, for example, WO 98/16636.

(3) Purification of a Target Protein

A reaction solution for protein synthesis obtained as described in the above section (2) is brought into contact with an affinity support which is used in the production of a cell extract for cell-free protein synthesis of the present invention or substantially the same affinity support, and then the protein which binds to the affinity support is eluted, thereby purifying the target protein with a high purity. The phrase "substantially the same affinity support" means that it is not required to be completely the same as far as it can bind to the same substance as the substance to which the affinity support used in the production of a cell extract for cell-free protein synthesis of the present invention binds and it has a property of adsorbing the synthesized protein. For the purification of a target protein using the affinity support, any known method suitable for each affinity support can be used. Addition of a compound having an imidazole ring such as 5 to 20 mM of imidazole, or a derivative thereof to a buffer for equilibrating the affinity support and to an elution buffer can avoid non-specific adsorption on the affinity support and can increase purification efficiency of the target protein.

After the adsorption on the affinity support, the target protein eluted by an appropriate method can be isolated, for example, by a SDS-polyacrylamide gel electrophoresis or the like and then confirmed by CBB staining or the like.

(4) Analysis of Interaction Between a Target Substance and a Protein

Further, a protein synthesized using the cell extract of the present invention can also be used in the analysis of the interaction between a protein and a substance. For instance, a support on which a target substance capable of binding to a protein is carried is used as an affinity support and is then brought into contact with a protein synthesized using the cell extract of the present invention, thereby the analysis of the interaction between the protein and the target substance can be analyzed. In this case, a single kind of protein may be synthesized and the interaction between the protein and the target substance carried on the support may be analyzed. Alternatively, a plurality of proteins, such as a protein library, may be synthesized and any protein that interacts with the target substance may be searched from these proteins. The method of analyzing the interaction is not particularly limited, and for example, a labeled protein is synthesized and the analysis may be carried out on the basis of the amount of a labeled substance that specifically binds to the support. In addition, a molecule as described above which has a form that a protein (polypeptide) is covalently bound to nucleic acids that encode the protein may be used. In this case, a protein that binds to the target substance can be easily identified, so that it is suitable for the study of searching a protein that interacts with a target substance.

EXAMPLES

Hereinafter, the present invention will be more specifically described with reference to examples. The examples as described below show only some embodiments of the present invention, and the scope of the present invention is not limited to the following examples.

In the following examples, "min" represents "minute(s)", "l" represents "liter", "ml" represents "milliliter", "M" represents "mole/liter", "mM" represents "millimole/liter", and "μg" represents "microgram", respectively.

Example 1

Fine Grinding Extraction with Waring Blender

Chihoku wheat (unsterilized) grown in Hokkaido was used and germ was then separated therefrom according to the method described in the examples of WO 02/295377, and, sorted until the purity of germ (in other words, weight ratio of germ contained in 1 g of a given sample) reaches to 98% or more. Subsequently, 50 g of the obtained wheat germ was suspended in distilled water at 4° C. and then washed with an ultrasonic cleaner until a washing solution no longer becomes cloudy. Subsequently, the germ was suspended in a solution of 0.5% by volume of Nonidet P40 and then washed with an ultrasonic cleaner until a washing solution no longer becomes cloudy, thereby obtaining endosperm components-free wheat germ.

Next, the following procedure was carried out at 4° C. to obtain a wheat germ extract. At first, the washed wheat germ was placed in a Waring blender together with 100 ml of extraction buffer (80 mM of HEPES-KOH (pH 7.8), 200 mM of potassium acetate, 10 mM of magnesium acetate, 4 mM of calcium chloride, 0.6 mM of each of 20 different L-amino acids, and 8 mM of dithiothreitol) and then ground at a rotational frequency of 5,000 to 20,000 rpm for 30 sec. The germ and the like attached to the inner wall of the blender were scraped off, and then ground again at 5,000 to 20,000 rpm for 30 sec twice. The particle-size distribution of the obtained ground germ product was determined using a laser-scattering measuring device for particle-size distribution (LA-920, Horiba, Ltd.).

A mixture of the resultant extract and the ground germ was transferred to a centrifuge tube and then centrifuged at 30,000 g for 30 min, followed by collecting a supernatant. Subsequently, the procedure of centrifugation at 30,000 g for 30 min to collect a supernatant was repeated five times, thereby obtaining a transparent supernatant. The obtained supernatant was subjected to a gel filtration with a Sephadex G-25 column previously equilibrated with a buffer (40 mM of HEPES-KOH (pH 7.8), 100 mM of potassium acetate, 5 mM of magnesium acetate, 0.3 mM of each of 20 different L-amino acids, and 4 mM of dithiothreitol). The obtained solution was centrifuged at 30,000 g for 12 min to collect a supernatant, followed by concentrating the supernatant through an ultrafilter membrane. The concentrated product was designated as a wheat germ extract. The concentration of the sample was adjusted so that the optical density (O.D.) of the sample at 260 nm ($A_{260}$) was in the range of 180 to 250 ($A_{260}/A_{280}$ is approximately 1.5) (hereinafter, also referred to as an "untreated extract").

Example 2

Treatment of Wheat Germ Extract with Talon Metal Affinity Resin Column (1) Equilibration of Talon Metal Affinity Resin Column 100 μl of 50% solution of a Talon Metal Affinity Resin (manufactured by Clontech, BD Biosciences) was added to a spin column and then centrifuged at 3,000 rpm for 1 min at 4° C. to remove a storage buffer from the column support. Subsequently, the storage buffer-free support was added with 500 μl of the buffer (40 mM of HEPES-KOH (pH 7.8), 100 mM of potassium acetate, 5 mM of magnesium acetate, 0.3 mM of each of 20 different L-amino acids, and 4 mM of dithiothreitol) used at the time of preparing the wheat germ extract, and then centrifuged at 3,000 rpm for 1 min at 4° C. to remove the buffer from the column support. This procedure was repeated three times to equilibrate the support.

(2) Treatment of Wheat Germ Extract Treatment with the Column

To the column support equilibrated in the above procedure (1), 50 μl of the wheat germ extract produced in Example 1 was added and then incubated at 26° C. for 30 min, thereby carrying out the adsorption of endogenous proteins of the wheat germ extract, which can be adsorbed on the Talon Metal Affinity Resin. After that, the resultant was centrifuged at 3,000 rpm for 1 min at 4° C. to produce the endogenous proteins-free wheat germ extract that had been adsorbed on the Talon Metal Affinity Resin (hereinafter, also referred to as an "extract treated with a Talon column").

(3) Adjustment of Liquid Composition of the Extract Treated with Talon Column and the Untreated Extract The liquid compositions of the extract treated with the Talon column under the above condition and the untreated extract produced in Example 1 were adjusted so as to be final concentrations of 30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.4 mg/ml of creatine kinase, 0.380 mM of spermidine, and 20 different L-amino acids (0.3 mM of each). Subsequently, the wheat germ extract having the adjusted liquid composition was adjusted so as to have 75 Abs of an optical density at 260 nm with a buffer (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.4 mg/ml of creatine kinase, 0.380 mM of spermidine, and 20 different L-amino acids (0.3 mM of each).

Example 3

Comparison of the Protein Synthetic Ability of the Extract Treated with Talon Column with that of the Untreated Extract To 40 μl of each of the two different wheat germ extracts prepared in Example 2, two kinds of mRNAs: (i) an mRNA that encodes a GFP gene; and (ii) an mRNA that encodes a gene sequence of 10 histidines on the amino terminal, a PreScission™ Protease (Amersham, Biosciences, Inc.) recognition sequence at the downstream thereof, and a gene from methionine at position 1 to glutamic acid at position 163 of a JSP-1 structural gene at the downstream thereof, were used to carry out protein synthesis.

(1) Preparation of a Template
  (i) N-His-JSP-1 (1-163)/pEU

An oligo DNA containing an SP6 promoter sequence and a ribosome-binding sequence in the order from 5' to 3' (SEQ ID NO: 1) was obtained by chemical synthesis. Further, a DNA fragment was amplified by PCR using JSP-1 (GenBank Accession No. AF424702) as a template, an oligo DNA containing a sequence encoding a histidine tag, a PreScission™ Protease (Amersham, Biosciences, Inc.) recognition sequence, and a 5'-end sequence of JSP-1 at the downstream thereof (SEQ ID NO: 2) as a 5'-sense primer, an oligo DNA capable of amplifying a fragment up to glutamic acid at position 163 of JSP-1 added with a SfiI site on its 5'-end (SEQ ID NO: 3) as a 3'-antisense primer. The obtained DNA fragment was digested with SfiI (hereinafter, also referred to as a "JSP-1 fragment").

An SP6 promoter sequence, an omega (Ω) sequence, and a multi-cloning site were removed from pEU3b (Sawasaki, T., et al., Proc. Natl. Acad. Sci. USA, 99(23), 14652-14657 (2002)), which is a vector for protein synthesis, and then the NaeI and SfiI sites were added to the vector. This vector was digested with NaeI and then ligated with the DNA fragment represented by SEQ ID NO: 1 obtained in the above procedure. The plasmid was designated as pEUblunt. The pEUblunt was digested with SmaI and SfiI, and then ligated with the above-mentioned JSP-1 fragment. The resultant plasmid was designated as N-His-JSP-1 (1-163)/pEU.

(ii) GFP/pEU

A plasmid containing a DNA sequence encoding a green fluorescent protein (GFP) (Plasmid-pCaMV35S-sGFP (S65T)-NOS3'(25), Haas, J. et al., Curr. Biol., 6(3), 315-324 (1996)) was used as a template and primers each having a nucleotide sequence shown in SEQ ID NOS: 4 and 5 were used to carry out PCR. The amplified DNA fragment was digested with SfiI and then ligated with the pEUblunt that had been digested with SmaI and SfiI. The resultant plasmid was designated as GFP/pEU.

(2) Protein Synthesis

Transcription was carried out by using GFP/pEU, N-His-JSP-1 (1-163)/pEU prepared in the above procedure (1) as a template and SP6 RNA polymerase (Promega, Inc.), and the resultant RNA was purified by ethanol precipitation by conventional methods.

A translation reaction solution (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.4 mg/ml creatine kinase, 0.380 mM of spermidine, and 20 µl of 20 different L-amino acids (0.3 mM of each)), which contains each of the above-mentioned mRNA at a concentration of 2.0 mg/ml with respect to 40 µl of each of two different wheat germ extracts prepared in Example 2, was prepared.

The translation reaction solution was placed in a dialysis membrane and then carried out protein synthesis reaction at 26° C. for 24 hours using a buffer (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.380 mM of spermidine, and 2.5 ml of 20 different L-amino acids (0.3 mM of each)) as an external dialysis solution.

1 µl of protein synthesis solution after reaction was separated by SDS-PAGE and a synthesized product was then analyzed by CBB staining. The results are shown in FIG. 1. In the figure, the lane 1 represents a marker, the lane 2 represents creatine kinase as a control, the lane 3 represents a reaction solution in which N-His-JSP-1 was synthesized by using the untreated extract, the lane 4 represents a reaction solution in which N-His-JSP-1 was synthesized by using the extract treated with a Talon column, the lane 5 represents a reaction solution in which GFP was synthesized by using the untreated extract, and the lane 6 represents a reaction solution in which GFP was synthesized by using the extract treated with Talon column. As is evident from the figure, the wheat germ extract treated with the Talon Metal Affinity Resin column did not show an extremely low synthetic ability but showed almost equal ability to that of the untreated wheat germ extract.

Example 4

Comparison of the Purification Using Talon Metal Affinity Resin (1) Purification of Protein Synthesis Reaction Solution Using Talon Metal Affinity Resin Column 50 µl of each of a reaction solution in which a synthesis reaction using an mRNA of N-His-JSP-1 (1-163) of Example 3 (2) as a template had been carried out by the extract treated with the Talon column and a reaction solution in which a synthesis reaction using an mRNA of N-His-JSP-1 (1-163) of Example 3 (2) as a template had been carried out by the untreated extract, was added to the Talon Metal Affinity Resin equilibrated by the same way as the procedure of Example 2 (1), and then incubated at 4° C. for 60 min to allow the protein synthesis reaction solution to be adsorbed on the Talon Metal Affinity Resin. Subsequently, the resultant was centrifuged at 3,000 rpm for 1 min at 4° C. After that, 500 µl of a wash buffer (30 mM of HEPES-KOH (pH 7.8), 300 mM of sodium chloride, 10% glycerol, 10 mM of imidazole, and 2 mM of β-mercaptoethanol) was added and then centrifuged at 3,000 rpm for 1 min at 4° C. to remove the buffer. This procedure was carried out three times, thereby washing proteins and the like nonspecifically adsorbed on the Talon Metal Affinity Resin. Then, 50 µl of elution buffer (30 mM of HEPES-KOH (pH 7.8), 300 mM of sodium chloride, 10% glycerol, 400 mM of imidazole, and 2 mM of β-mercaptoethanol) was added to the above-mentioned column support and then incubated at 4° C. for 10 min, thereby eluting a protein adsorbed on the Talon Metal Affinity Resin.

Figure 2:
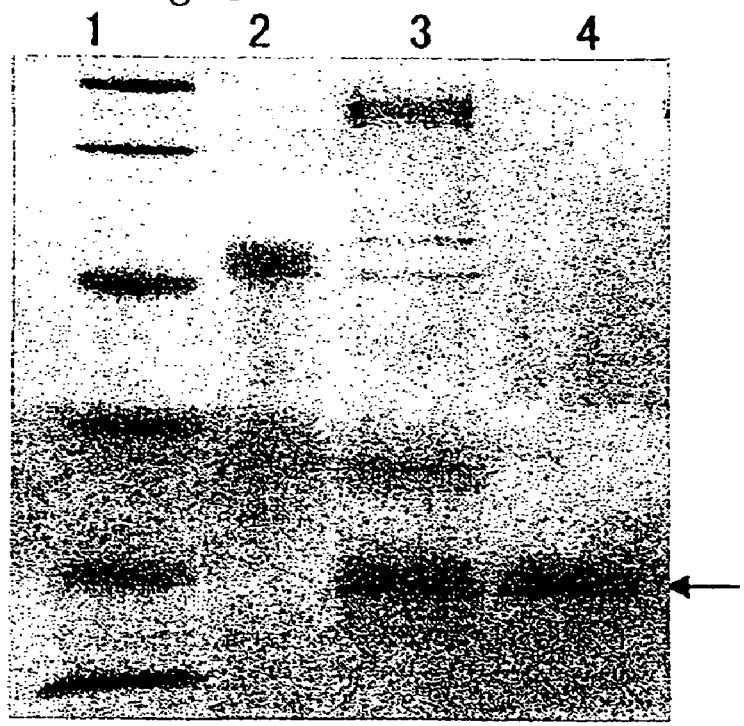
FIG. 2 is an electrophoretic photograph that shows proteins purified by a Talon column after carrying out the protein synthesis reaction by using the wheat germ extract treated with the same Talon column or the untreated wheat germ extract. In the figure, lane 1 represents a molecular marker, lane 2 represents creatine kinase as a control, lane 3 represents a result obtained by synthesizing the above protein using the untreated wheat germ extract and then purifying N-His-JSP-1 using the same metal ion immobilized support, and lane 4 represents a result obtained by synthesizing the above protein using the wheat germ extract treated with the Talon column and then purifying N-His-JSP-1 by using the same metal ion immobilized support. In a case where the protein synthesized by using the wheat germ extract treated with the Talon column is purified using the same support column, it is found that the purification efficiency of the target protein is extremely higher than that of the untreated wheat germ extract.

1 µl of the eluent as described above was separated by SDS-PAGE and then stained with CBB to analyze the purity of each protein. The results are shown in FIG. 2. In the figure, the lane 1 represents a molecular marker, the lane 2 represents creatine kinase as a control, the lane 3 represents a result obtained by carrying out purification with a Talon Metal Affinity Resin column after protein synthesis using the untreated extract, and the lane 4 represents a result obtained by carrying out the purification with a Talon column after the protein synthesis using the extract treated with the same column.

As is evident from these results, in the case where the protein synthesized using the extract treated with the Talon column was purified with the Talon Metal Affinity Resin column, the resultant protein contains only the target protein, while the results obtained by purifying the protein synthesized using the extract untreated with the Talon Metal Affinity Resin column showed that proteins derived from the wheat germ extract other than the target protein were contained in the eluent. From these results, it was confirmed that the target protein can be purified at an extremely high level by carrying out the purification of the protein synthesized by the extract treated with the Talon column, by using the Talon Metal Affinity Resin column.

Example 5

Treatment of Wheat Germ Extract with Ni-NTA Column (1) Equilibration of Ni-NTA Column 100 µl of 50% solution of Ni-NTA, which is a metal ion immobilized column support (QIAGEN), was added to a spin column and then centrifuged at 3,000 rpm for 1 min at 4° C. to remove the storage buffer from the column support. Next, to the storage buffer-free support, 500 μl of buffer (40 mM of HEPES-KOH (pH 7.8), 100 mM of potassium acetate, 5 mM of magnesium acetate, 0.3 mM of each of 20 different L-amino acids, 1 mM of dithiothreitol, and 10 mM of imidazole), which had been used for producing a wheat germ extract, was added and then centrifuged at 3,000 rpm for 1 min at 4° C. to remove the buffer. This procedure was repeated three times to equilibrate the support.

(2) Treatment of Wheat Germ Extract with Ni-NTA Column

To the column support equilibrated in the above-mentioned section (1), a mixture prepared by adding 10 mM of imidazole to 50 μl of the wheat germ extract produced in Example 1 was applied and then incubated for 30 min at 4° C. to carry out the adsorption of endogenous proteins of the wheat germ extract which can be adsorbed on the Ni-NTA column. Subsequently, the resultant was centrifuged at 3,000 rpm for 1 min at 4° C., thereby producing the endogenous proteins-free wheat germ extract which can be adsorbed on the Ni-NTA column (hereinafter, also referred to as an "extract treated with a Ni-NTA column").

(3) Adjustments of the Liquid Composition of the Extract Treated with Ni-NTA Column and the Untreated Extract The liquid compositions of the extract treated with Ni-NTA column produced under the above-mentioned condition and the untreated extract produced in Example 1 were adjusted so as to be final concentrations of 30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.4 mg/ml of creatine kinase, 0.380 mM of spermidine, and 20 different L-amino acids (0.3 mM of each). Subsequently, the wheat germ extract having the adjusted liquid composition was adjusted so as to have 75 Abs of an optical density at 260 nm using a buffer (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.6 mg/ml of creatine kinase, 0.380 mM of spermidine, and 20 different L-amino acids (0.3 mM of each).

Example 6

Comparison of Protein Synthetic Ability of the Extract Treated with Ni-NTA Column with that of the Untreated Extract To 40 μl of each of two different wheat germ extracts prepared in Example 5, two kinds of mRNAs: (i) an mRNA that encodes a gene of Protein Kinase 65 (SEQ ID NO: 6) added with a sequence of 10 histidines at a downstream thereof; and (ii) an mRNA that encodes a structural gene of Protein Kinase 142 (helix clone) added with a sequence of 10 histidines at a downstream thereof were used to carry out protein synthesis.

(1) Preparation of a Template (i) Protein Kinase 65-CHIS/pEU

A DNA fragment was amplified by PCR using Protein Kinase 65 (SEQ ID NO: 6) as a template, an oligo DNA containing a 5'-end sequence of the Protein Kinase 65 (SEQ ID NO: 7) as a 5'-sense primer, and an oligo DNA which was added with SfiI site to the 5'-end and added with a sequence encoding a histidine tag, and can amplify Protein Kinase 65 containing no termination codon (SEQ ID NO: 8) as a 3'-antisense primer. The obtained DNA fragment was digested with SfiI (hereinafter, also referred to as a "PK65 fragment"). Subsequently, the pEUblunt as described in the procedure (i) of Example 3 (1) was digested with SmaI and SfiI, and then ligated with the PK65 fragment. The obtained plasmid was designated as Protein Kinase 65-CHIS/pEU.

(ii) Protein Kinase 142-CHIS/pEU

A DNA fragment was amplified by PCR using Protein Kinase 142 (SEQ ID NO: 9) as a template, an oligo DNA containing a 5'-end sequence of the Protein Kinase 142 at the downstream thereof (SEQ ID NO: 10) as a 5'-sense primer, and an oligo DNA which was added with SfiI site to the 5'-end and added with a sequence coding a histidine tag, and can amplify Protein Kinase 142 containing no termination codon (SEQ ID NO: 11) as a 3'-antisense primer. The obtained DNA fragment was digested with SfiI (hereinafter, also referred to as a "PK142 fragment"). Subsequently, the pEUblunt as described in the procedure (i) of Example 3 (1) was digested with SmaI and SfiI, and then ligated with the PK142 fragment. The obtained plasmid was designated as Protein Kinase 142-CHIS/pEU.

(2) Protein Synthesis

Transcription was carried out by using Protein Kinase 142-CHIS/pEU or Protein Kinase 65-CHIS/pEU which had been prepared in the above-mentioned procedure (1) as a template, and using SP6 RNA polymerase (Promega), and the obtained RNA was purified by an ethanol precipitation according to the usual methods.

A translation reaction solution (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.6 mg/ml creatine kinase, 0.380 mM of spermidine, and 20 μl of 20 different L-amino acids (0.3 mM of each)), which contains each of the above-mentioned mRNA at a concentration of 2.0 mg/ml with respect to 40 μl of each of two different wheat germ extracts prepared in Example 5, was prepared.

The translation reaction solution was placed in a dialysis membrane and then protein synthesis reaction was carried out at 26° C. for 24 hours using a buffer (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.380 mM of spermidine, and 2.5 ml of 20 different L-amino acids (0.3 mM of each)) as an external dialysis solution.

The amount of the target protein in the respective reaction solution for protein synthesis was compared with each other by the method as described in Example 3(2). As a result, the protein synthetic ability of the extract treated with the Ni-NTA column was almost equal to that of the untreated extract.

Example 7

Comparison of the Purification with Ni-NTA Column of the Respective Reaction Solutions for Protein Synthesis (1) Purification of the Protein Synthesis Reaction Solution Using Ni-NTA Column 50 μl of each of the reaction solution in which synthesis reaction with an mRNA of Protein Kinase 65-CHIS or Protein Kinase 142-CHIS of Example 6 (2) as a template had been carried out using the extract treated with the Ni-NTA column and the reaction solution in which synthesis reaction with an mRNA of Protein Kinase 65-CHIS or Protein Kinase 142-CHIS of Example 6 (2) as a template had been carried out using an untreated extract was added to the Ni-NTA column equilibrated by the same way as the procedure of Example 5 (1), and then incubated at 4° C. for 60 min to allow the protein synthesis reaction solution to be adsorbed on the Ni-NTA column. Subsequently, the resultant was centrifuged at 3,000 rpm for 1 min at 4° C. After that, 500 µl of wash buffer (30 mM of HEPES-KOH (pH 7.8), 300 mM of sodium chloride, 10% glycerol, 10 mM of imidazole, and 1 mM of dithiothreitol) was added and then centrifuged at 3,000 rpm for 1 min at 4° C. to remove the buffer. This procedure was carried out three times, thereby washing proteins and the like that were non-specifically adsorbed on the support. Then, 50 µl of elution buffer (30 mM of HEPES-KOH (pH 7.8), 300 mM of sodium chloride, 10% glycerol, 200 mM of imidazole, and 1 mM of dithiothreitol) was added to the above-mentioned column support and then incubated at 4° C. for 10 min, thereby eluting a protein adsorbed on the Ni-NTA column.

Figure 3:
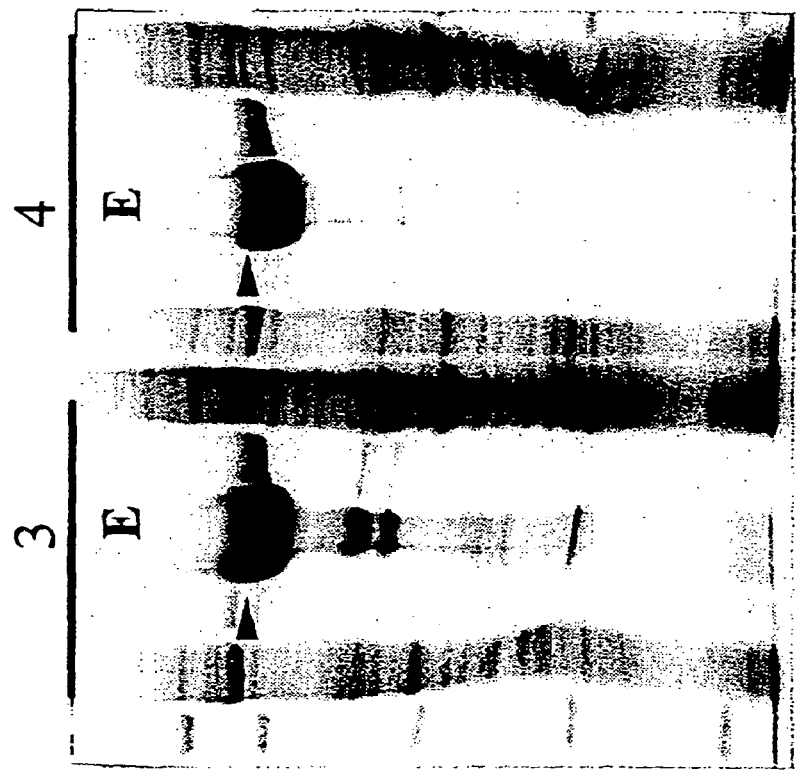
FIG. 3 is an electrophoretic photograph that shows proteins purified by a Ni-NTA column after carrying out a protein synthesis reaction by using the wheat germ extract treated with the same Ni-NTA column or the untreated wheat germ extract. In the figure, lane 1 represents a result obtained by synthesizing the above protein using the untreated extract and then purifying PK65 using a Ni-NTA column, lane 2 represents a result obtained by synthesizing the above protein using the extract treated with the same Ni-NTA column and then purifying PK65 using a Ni-NTA column, lane 3 represents a result obtained by synthesizing the above protein using the untreated extract and then purifying PK142 using a Ni-NTA column, and lane 4 represents a result obtained by synthesizing the above protein using the extract treated with the same Ni-NTA column and then purifying PK142 using a Ni-NTA column. In the result that the protein synthesized using the extract treated with the Ni-NTA column is purified by the Ni-NTA column, it is found that the purity of the target protein in an eluent is high. On the other hand, in the result that the protein synthesized using the untreated extract was purified by the Ni-NTA column, it is found that, in addition to the target protein, proteins derived from the wheat germ extract were contained in an eluent at high concentration. In other words, it is confirmed that the target protein can be purified to an extremely high degree by purifying the protein, which is synthesized using the extract treated with Ni-NTA column, with the Ni-NTA column.
Figure 3:
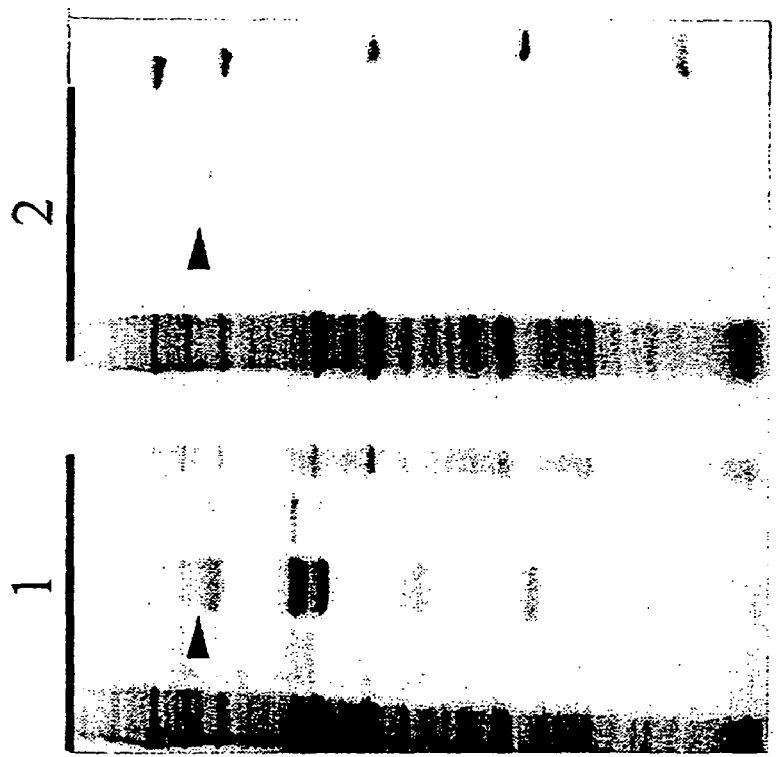

1 µl of the eluent as described above was separated by SDS-PAGE and then stained with CBB to analyze the purity of each protein. The results are shown in FIG. 3. In the figure, the lane 1 represents a result obtained by carrying out the purification with the Ni-NTA column after the synthesis of PK65 using the untreated extract, the lane 2 represents a result obtained by carrying out the purification with the a Ni-NTA column after the synthesis of PK65 using the extract treated with the same Ni-NTA column, the lane 3 represents a result obtained by carrying the purification with the Ni-NTA column after the synthesis of PK142 using the untreated extract, and the lane 4 represents a result obtained by carrying out the purification with the Ni-NTA column after the synthesis of PK142 using the extract treated with the same Ni-NTA column.

As is evident from these results, in the case where the protein synthesized using the extract treated with the Ni-NTA column was purified with the Ni-NTA column, the purity of the target protein in the eluent is high, while, in the case where the protein synthesized using the untreated extract was purified with the Ni-NTA column, it was found that proteins derived from the wheat germ extract other than the target protein were contained in the eluent at high concentration. From these results, it was confirmed that the target protein can be purified at an extremely high level by carrying out the purification of the protein, which has been synthesized by the extract treated with the Ni-NTA column, by using Ni-NTA column.

Example 8

Treatment of Wheat Germ Extract with a Glutathione-Immobilized Support (1) Equilibration of a Glutathione-Immobilized Support Column 50 µl of MicroSpin GST Purification Module, which is a glutathione-immobilized support (Amersham, Biosciences), was added to a column and then centrifuged at 3,000 rpm for 1 min at 4° C. to remove the storage buffer from the column. Next, to the storage buffer-free support, 500 µl of the buffer (40 mM of HEPES-KOH (pH 7.8), 100 mM of potassium acetate, 5 mM of magnesium acetate, 0.3 mM of each of 20 different L-amino acids, and 2.5 mM of dithiothreitol), which had been used for preparing the wheat germ extract, was added and then centrifuged at 3,000 rpm for 1 min at 4° C. to remove the buffer. This procedure was repeated three times to equilibrate the support.

(2) Treatment of Wheat Germ Extract with Glutathione-Immobilized Support Column

To the column support equilibrated in the above-mentioned section (1), 50 µl of the wheat germ extract produced in Example 1 was applied and then incubated at 4° C. for 30 min to carry out the adsorption of endogenous proteins of the wheat germ extract, which can be adsorbed on a glutathione-immobilized support column. Subsequently, the resultant was centrifuged at 3,000 rpm for 1 min at 4° C., thereby preparing the endogenous proteins-free wheat germ extract to be adsorbed on the glutathione-immobilized support column (hereinafter, also referred to as an "extract treated with a glutathione-immobilized support).

(3) Adjustments of Liquid Composition of the Extract Treated with the Glutathione-Immobilized Support and the Untreated Extract The liquid compositions of the extract treated with the glutathione-immobilized support prepared under the above-mentioned condition and the untreated extract prepared in Example 1 were adjusted so as to be final concentrations of 30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.4 mg/ml of creatine kinase, 0.380 mM of spermidine, and 20 different L-amino acids (0.3 mM of each). Subsequently, the wheat germ extract having the adjusted liquid composition was adjusted so as to have 75 Abs of an optical density at 260 nm using a buffer (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.4 mg/ml of creatine kinase, 0.380 mM of spermidine, and 20 different L-amino acids (0.3 mM of each)).

Example 9

Comparison of Protein Synthetic Ability of the Extract Treated with Glutathione-Immobilized Support with that of the Untreated Extract To 40 µl of each of two different wheat germ extracts prepared in Example 8, protein synthesis was carried out using (i) an mRNA that encodes a structural gene of GFP added with a gene sequence of GST at the upstream thereof.

(1) Preparation of a Template
(i) NGST-GFP/pEU

A DNA fragment was amplified by PCR using GST (SEQ ID NO: 12) as a template, an oligo DNA containing a 5'-end sequence of GST (SEQ ID NO:13) as a 5'-sense primer, and an oligo DNA which was added with a sequence annealing to the 5'-end of GFP at the 5'-end, and can amplify GST containing no terminal codon (SEQ ID NO:14) as a 3'-antisense primer. A DNA fragment was amplified by PCR using the obtained DNA fragment and the GFP fragment produced in Example 3 as templates, the oligo DNA containing a sequence of GST (SEQ ID NO:13) as a 5'-sense primer, and the oligo DNA containing a sequence of GFP added with SfiI sequence at 5'-end (SEQ ID NO:5) as a 3'-antisense primer. The obtained DNA fragment was digested with SfiI (hereinafter, also referred to as a "GST-GFP fragment"). pEUblunt as described in the procedure (i) of Example 3 (1) was digested with SmaI and SfiI, and then ligated with the above-mentioned GST-GFP fragment. The obtained plasmid was designated as NGST-GFP/pEU.

(2) Protein Synthesis

Transcription was carried out by using NGST-GFP/pEU prepared in the above-mentioned procedure (1) as a template and using SP6 RNA polymerase (manufactured by Promega, Inc.), and the obtained RNA was purified by an ethanol precipitation according to a usual method.

A translation reaction solution (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.4 mg/ml creatine kinase, 0.380 mM of spermidine, and 20 µl of 20 different L-amino acids (0.3 mM of each)), which contains each of the above-mentioned mRNA at a concentration of 2.0 mg/ml with respect to 40 µl of each of two different wheat germ extracts prepared in Example 8, was prepared.

The translation reaction solution was placed in a dialysis membrane and then protein synthesis reaction was carried out at 26° C. for 24 hours using a buffer (30 mM of HEPES-KOH, pH 7.8, 100 mM of potassium acetate, 2.65 mM of magnesium acetate, 2.5 mM of dithiothreitol, 1.2 mM of ATP, 0.25 mM of GTP, 16 mM of creatine phosphate, 0.380 mM of spermidine, and 2.5 ml of 20 different L-amino acids (0.3 mM of each)) as an external dialysis solution.

The amounts of target proteins in the respective reaction solutions for protein synthesis were compared with each other by the method as described in Example 3(2). As a result, the protein synthetic ability of the extract treated with the glutathione-immobilized support was almost equal to that of the untreated extract.

Example 10

Comparison of Purification of the Protein Synthesis Reaction Solution with a Glutathione-Immobilized Support Column (1) Purification of Reaction Solution for Protein Synthesis with a Glutathione-Immobilized Support Column 50 µl of each of a reaction solution in which the synthesis reaction using an mRNA of GST-GFP as a template had been carried out with an extract treated with the glutathione-immobilized support in Example 9(2) or a reaction solution in which the synthesis reaction using an mRNA of GST-GFP as a template had been carried out in of Example 9(2) with an untreated extract was added to the glutathione-immobilized support column equilibrated by the same way as the procedure of Example 8 (1), followed by allowing the protein synthesis reaction solution to be adsorbed on the support according to the protocol of MicroSpin GST Purification Module (Amersham Biosciences, Inc.). Subsequently, proteins and the like which were non-specifically adsorbed on the support were washed and eluted according to the protocol of MicroSpin GST Purification Module (Amersham Biosciences, Inc.).

5 µl of the eluent as described above was separated by SDS-PAGE and then stained with CBB to analyze the purity of target protein. From the result, in the case where the protein synthesized by using the extract treated with the glutathione-immobilized support column was purified with the same glutathione-immobilized column, the purity of the target protein was slightly higher as compared with the case using the untreated extract. Further, according to the result obtained by purifying the target protein, which had been synthesized using the untreated extract, with the glutathione-immobilized support column, it was found that a small amount of proteins derived from the wheat germ extract was contained in the eluent, in addition to the target protein.

INDUSTRIAL APPLICABILITY

A target protein of high purity can be obtained by carrying out protein synthesis by using a cell extract for cell-free protein synthesis, which has been improved by the present invention, and then purifying the protein by using the affinity support which has been used in the production of the cell extract. According to such a method, because a bed volume of the affinity support column can be reduced, the target protein can also be concentrated, and thus, it is very advantageous to collect a protein synthesized in a small amount in a cell-free protein synthetic system. Further, it becomes possible to supply a large amount of a highly-purified target protein for structural and functional analysis of protein, where a highly-purified protein is required.

Still further, it becomes possible to significantly reduce the ratio of pseudo-positives and carry out an interaction analysis at higher efficiency in a case where the analysis of the interaction between a protein and a substance is carried out by performing the protein synthesis using a cell extract for cell-free protein synthesis, which has been improved by the present invention, and contacting the protein with an affinity support which is substantially the same affinity support as one used in the production of the cell extract to select a protein which has an affinity to a substance retained on the affinity support and binds to the substance.

The invention claimed is:

1. A method of purifying a protein of interest, comprising:
a) providing a cell extract capable of synthesis of a protein of interest and a first affinity support;
b) contacting the cell extract prior to synthesis of the protein of interest with the first affinity support, and thereby removing substances bound to the first affinity support from the cell extract;
c) removing the first affinity support with the substances bound thereto from the cell extract;
d) synthesizing the protein of interest by contacting the cell extract of step c) and mRNA; and
e) contacting the cell extract of step d) with a second affinity support substantially the same as the first affinity support, and thereby binding and purifying the protein of interest.

2. The method according to claim 1, wherein the cell extract is a wheat germ extract.

3. The method according to claim 1, wherein the first and second affinity supports are metal ion immobilized supports.

4. The method according to claim 3, wherein the metal ion immobilized supports are cobalt immobilized supports, nickel immobilized supports, or zinc immobilized supports.

5. The method according to claim 1, wherein the affinity supports are glutathione immobilized supports.

* * * * *

UNITED STATES PATENT AND TRADEMARK OFFICE
CERTIFICATE OF CORRECTION

| | | |
|---|---|---|
| PATENT NO. | : 7,838,640 B2 | Page 1 of 1 |
| APPLICATION NO. | : 10/591754 | |
| DATED | : November 23, 2010 | |
| INVENTOR(S) | : Yoshiko Yoshiyama et al. | |

It is certified that error appears in the above-identified patent and that said Letters Patent is hereby corrected as shown below:

TITLE PAGE

Item (73), Assignee, "Cellfree Sciences Co., Ltd., Kanagawa (JP)" should read -- CellFree Sciences Co., Ltd., Kanagawa (JP)--.

Signed and Sealed this
Seventh Day of August, 2012

David J. Kappos
*Director of the United States Patent and Trademark Office*

SEQUENCE LISTING

<160> NUMBER OF SEQ ID NOS: 14

<210> SEQ ID NO 1
<211> LENGTH: 98
<212> TYPE: DNA
<213> ORGANISM: Artificial
<220> FEATURE:
<223> OTHER INFORMATION: synthetic

<400> SEQUENCE: 1

```
gccggccgat ttaggtgaca ctatagaaca tcaacatctt acattttaca ttataatttt      60
cactctctat ttttttttac attaacaaca tttttagg                              98
```

```
<210> SEQ ID NO 2
<211> LENGTH: 89
<212> TYPE: DNA
<213> ORGANISM: Artificial
<220> FEATURE:
<223> OTHER INFORMATION: synthetic

<400> SEQUENCE: 2
atgcatcatc atcatcatca tcatcatcat catagcagcg gccatctgga agttctgttc      60
cagggcccta tggggaatgg gatgaacaa                                        89

<210> SEQ ID NO 3
<211> LENGTH: 36
<212> TYPE: DNA
<213> ORGANISM: Artificial
<220> FEATURE:
<223> OTHER INFORMATION: synthetic

<400> SEQUENCE: 3 ggccttttg gcctcattct gcatcctgca aagggc                                 36

<210> SEQ ID NO 4
<211> LENGTH: 20
<212> TYPE: DNA
<213> ORGANISM: Artificial
<220> FEATURE:
<223> OTHER INFORMATION: synthetic

<400> SEQUENCE: 4
atggtgagca agggcgagga                                                  20

<210> SEQ ID NO 5
<211> LENGTH: 33
<212> TYPE: DNA
<213> ORGANISM: Artificial
<220> FEATURE:
<223> OTHER INFORMATION: synthetic

<400> SEQUENCE: 5 ggccttttg gccttacttg tacagctcgt cca                                    33

<210> SEQ ID NO 6
<211> LENGTH: 1731
<212> TYPE: DNA
<213> ORGANISM: Homo sapiens

<400> SEQUENCE: 6
atgaggcacc agggggaagat ccccgaggag ctttcactag atgacagagc gaggacccag     60
aagaagtggg ggagggggaa atgggagcca gaacccagta gcaagccccc cagggaagcc    120
actctggaag agaggcacgc aaggggagag aagcatcttg gggtggagat tgaaaagacc    180
tcgggtgaaa ttatcagatg cgagaagtgc aagagagaga gggagctcca gcagagcctg    240
gagcgtgaga ggcttttctct ggggaccagt gagctggata tggggaaggg cccaatgtat    300
gatgtggaga agctggtgag gaccagaagc tgcaggaggt ctcccgaggc aaatcctgca    360
agtggggagg aagggtggaa gggtgacagc cacaggagca gccccaggaa tcccactcaa    420
gagctgagga gacccagcaa gagcatggac aagaaagagg acagaggccc agaggatcaa    480
gaaagccatg ctcagggagc agccaaggcc aagaaggacc ttgtggaagt tcttcctgtc    540
acagaggagg ggctgaggga ggtgaagaag acaccaggc ccatgagcag agcaaaacat    600
ggtggctggc tcctgagaga gcaccaggcg ggctttgaga agctccgcag gacccgagga    660
```

```
gaagagaagg aggcagagaa ggagaaaaag ccatgtatgt ctggaggcag aaggatgact    720
ctcagagatg accaacctgc aaagctagaa aaggagccca agacgaggcc agaagagaac    780
aagccagagc ggcccagcgg tcggaagcca cggcccatgg gcatcattgc cgccaatgtg    840
gaaaagcatt atgagactgg ccgggtcatt ggggatggga actttgctgt cgtgaaggag    900
tgcagacacc gcgagaccag gcaggcctat gcgatgaaga tcattgacaa gtccagactc    960
aagggcaagg aggacatggt ggacagtgag atcttgatca tccagagcct ctctcacccc   1020
aacatcgtga aattgcatga agtctacgaa acagacatgg aaatctacct gatcctggag   1080
tacgtgcagg gaggagacct ttttgacgcc atcatagaaa gtgtgaagtt cccggagccc   1140
gatgctgccc tcatgatcat ggacttatgc aaagccctcg tccacatgca cgacaagagc   1200
attgtccacc gggacctcaa gccggaaaac cttttggttc agcgaaatga ggacaaatct   1260
actaccttga aattggctga ttttggactt gcaaagcatg tggtgagacc tatatttact   1320
gtgtgtggga ccccaactta cgtagctccc gaaattcttt ctgagaaagg ttatggactg   1380
gaggtggaca tgtgggctgc tggcgtgatc ctctatatcc tgctgtgtgg ctttcccca    1440 ttccgcagcc tgagaggga ccaggacgag ctctttaaca tcatccagct gggccacttt   1500
gagttcctcc cccttactg ggacaatatc tctgatgctg ctaaagatct ggtgagccgg   1560
ttgctggtgg tagaccccaa aaagcgctac acagctcatc aggttcttca gcaccctgg   1620 atcgaaacag ctggcaagac caatacagtg aaacgacaga agcaggtgtc ccccagcagc   1680
gagggtcact tccggagcca gcacaagagg gttgtggagc aggtatcata g            1731

<210> SEQ ID NO 7
<211> LENGTH: 18
<212> TYPE: DNA
<213> ORGANISM: Artificial
<220> FEATURE:
<223> OTHER INFORMATION: synthetic

<400> SEQUENCE: 7
atgaggcacc aggggaag                                                   18

<210> SEQ ID NO 8
<211> LENGTH: 64
<212> TYPE: DNA
<213> ORGANISM: Artificial
<220> FEATURE:
<223> OTHER INFORMATION: synthetic

<400> SEQUENCE: 8
ggccattaag gcctcaatgg tgatggtgat ggtgatggtg atggtgatac ctgctccaca     60
accc                                                                  64

<210> SEQ ID NO 9
<211> LENGTH: 2121
<212> TYPE: DNA
<213> ORGANISM: Homo sapiens

<400> SEQUENCE: 9
atggaggaca ggaaggagct cttaacggaa atcccggttg cggaattat aaagaagaac      60 ggagagaagt acattacgga gctggacgag accaagacca agatcgtgga ccgctatcgc    120
gttgggaagc agatcggcaa gggtgggttt gcgattgtgt atgagctgac gagcattcgg    180
acggggaaga agtacgcggg caaggtggtg gagaaggcgg gcctgaccaa gcccaagtat    240
ctcgagaagt tcatgagcga aatccggatt caccagtcgc tggaccatcc ccacatctgc    300
```

-continued

```
aagatgtaca agcactttga ggataatcgc taccactacc tcattctgga gttgtgttcg    360
aacgagacgc tggcgcatct gcttcgcgtc cgggagtgcc tcaccgagcc ggaggtacag    420 tacttttgc tgcagatcat cgacgcggtg agctacctcc acaagcgctg catcatccac     480
cgcgatctca aattgggcaa catcttcctc gacgagaacc tggaggtgaa ggtgggcgac    540
ctgggtctcg cggcgcagct gaacgagccg aacgagcgca agaagacgat gtgcggcact    600
ccgaactaca tcgcaccgga gattttgcag tcgaacgaca agcgcgccta ctcctacgag    660
gtggacatct gggcggtcgg cgtgatcacc tacacgatgc tgatcggcaa ggcgccgttc    720
gacggcggca gcaaggagat cacctaccgc aagatccgcg agaacgagct gtcctttccc    780
atcaaggacc accacatttc ccaccaagcg cgcatgttca tccggtcgat cctcaacccc    840
gaccccacgc agcgcctcac gctggagcag atggtacagc accccttctt caccgactcg    900
cccatcgacc cgcccaagtc gctgccgctc tacatcctgc gcgagccctt cctcctctcc    960
gcgcgcctcc ccaccgagcc cacgcccgta ctccagcggg cgcagcgcct ccccgccgag   1020
gacaccggcg tcggcgaggc caagcgcatc cgcatggccg acctccccgc gccgcggctc   1080
cctgcgcctg ctactgtgtc ttctccttct cctgcagtgg gtactgtggg tcaggcaaca   1140
ggcgaggtgg gcggcaacgc gtacacagcg cacctcttcc gcccgcaggc ggcggagtac   1200
gacctggacg gcaatgggcg caacaacctg aaccgcttct cgctgacggg cgaccgcgcg   1260
cgtgagatgg agggccggct ggactacgtg aaccgctcct tccacgacgc gcgcgggctg   1320
ctgccgtcgg aggtgttcga gggcctgccg acgggcatcg tgcctccat caccgtcccg    1380 cggggacgct tcgaggagaa ggaggggtcg ccgctgctgc aggcgcacgc agccaatctg   1440
tacacggcga tgaacaaccc gggactgatg gtgccggcga accacgtaca ggtgactcgc   1500
acagcgaact ggatcgtgga cgagtacgac ttcacgcgga agtacgggat cgggtacatg   1560
ttcagcaacg gcaacatcgg catcctgttc aacgacaaga cctccatcgt gctgtcggcg   1620
gacggcatgt tcttcgagta ccacccacgc atctcgatca cgcagtggaa cgccaagcag   1680
acgttcccgc cgtcggtgtc gggtagcatc gacgattacc ccgacgagct ggcgaagaag   1740
atcacgctga tcaagtactt ccgcaccaat ttccgagatc gtgcggagaa ccgcatgctg   1800
tcgaaggagg aggtggagga cacggcgcgc ggcgggccga aggtgaacat gccgttcgcg   1860
ctgaagtggc tgaagaagga ggacgcgtcg atctgcatgc tgagcacggg cgccattcag   1920
gtgcgctacg atggaggcac catcctgaac ttggagagtc cgttcgacga cgtgacgtat   1980
ttggacaagt acggtgtcgt gaccgccatg ccgctggcga gggccatctc gctcaagaga   2040
gacgatctca tgcggcgctt ggactacgtg gagagcaaca tccaggacat cgtgacgcac   2100
ctcagcaagg cccatcatta a                                             2121
```

<210> SEQ ID NO 10
<211> LENGTH: 19
<212> TYPE: DNA
<213> ORGANISM: Artificial
<220> FEATURE:
<223> OTHER INFORMATION: synthetic

<400> SEQUENCE: 10

```
atggaggaca ggaaggagc                                                  19
```

<210> SEQ ID NO 11
<211> LENGTH: 65
<212> TYPE: DNA
<213> ORGANISM: Artificial
<220> FEATURE:
<223> OTHER INFORMATION: synthetic

<400> SEQUENCE: 11
ggccattaag gcctcaatgg tgatggtgat ggtgatggtg atggtgatga tgggccttgc    60
tgagg                                                               65

<210> SEQ ID NO 12
<211> LENGTH: 657
<212> TYPE: DNA
<213> ORGANISM: Schistosoma japonicum

<400> SEQUENCE: 12
atgtccccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca    600 tggcctttgc agggctggca agccacgttt ggtggtggcg accatcctcc aaaataa      657

<210> SEQ ID NO 13
<211> LENGTH: 27
<212> TYPE: DNA
<213> ORGANISM: Artificial
<220> FEATURE:
<223> OTHER INFORMATION: synthetic

<400> SEQUENCE: 13
atgtccccta tactaggtta ttggaaa                                        27

<210> SEQ ID NO 14
<211> LENGTH: 39
<212> TYPE: DNA
<213> ORGANISM: Artificial
<220> FEATURE:
<223> OTHER INFORMATION: synthetic

<400> SEQUENCE: 14
tcctcgccct tgctcaccat ttttggagga tggtcgcca                           39